United States Patent [19]

Green et al.

[11] Patent Number: 4,719,120

[45] Date of Patent: Jan. 12, 1988

[54] DETECTION OF OXYGEN IN THIN FILMS

[75] Inventors: Arold K. Green, Ridgecrest; Robert H. Hammond, Palo Alto, both of Calif.

[73] Assignee: The United States of America as represented by the Secretary of the Navy, Washington, D.C.

[21] Appl. No.: 913,793

[22] Filed: Sep. 29, 1986

[51] Int. Cl.$^4$ .............................................. B05D 5/12
[52] U.S. Cl. ........................................ 427/8; 427/250; 427/255.2; 427/255.3; 427/255.7; 427/404; 427/419.2
[58] Field of Search .................. 427/8, 62, 250, 255.2, 427/255.3, 255.7, 404, 419.2

[56] References Cited

U.S. PATENT DOCUMENTS

| | | | |
|---|---|---|---|
| 3,279,888 | 10/1966 | Holler | 23/230 |
| 3,401,261 | 9/1968 | Fuchs | 250/49.5 |
| 3,461,306 | 8/1969 | Stout et al. | 250/49.5 |
| 3,490,873 | 1/1970 | Corl | 23/230 |
| 3,916,190 | 10/1975 | Valentine et al. | 250/305 |
| 4,287,224 | 9/1981 | Heimbach et al. | 427/8 |
| 4,348,886 | 9/1982 | Faith, Jr. | 73/19 |
| 4,412,902 | 11/1983 | Michikami et al. | 427/62 |
| 4,458,409 | 7/1984 | Latta et al. | 427/62 |

FOREIGN PATENT DOCUMENTS 681357  8/1979  U.S.S.R. .................... 427/8

Primary Examiner—Sadie L. Childs
Attorney, Agent, or Firm—William C. Townsend; W. Thom Skeer; Stephen J. Church

[57] ABSTRACT

A method for determining the presence, during deposition of a first thin film layer, of a substance which escapes when the layer is cooled and transferred from its deposition environment for analysis to determine the presence of the substance. The layer is first covered with a second layer of a material which captures the escaping substance. This second layer is then covered with a cap layer of a substance which seals the second layer against contamination, as from the atmosphere during transfer. The layered structure, with the escaped substance retained in the second layer, is then analyzed, as by sputter depth profiling and Auger electron spectroscopy, to determine the presence in the second layer of the escaped substance and thus determine the presence of this substance during deposition of the first layer.

7 Claims, 3 Drawing Figures

DETECTION OF OXYGEN IN THIN FILMS

BACKGROUND OF THE INVENTION

1. Field of the Invention

This invention pertains to the field of measurement and testing. More particularly, the invention pertains to measurement of the gas content of material.

2. Description of the Prior Art

In the formation of a thin film of a desired material it is frequently necessary that a specific substance be present during deposition of the film to produce the material. When the film is brought to different conditions than those at which the film was deposited, this substance escapes from the film before the film can be analyzed for the substance. As a result, it is not only difficult to determine that the substance was present in the film during deposition thereof, but it may be impossible to determine that the presence of such a substance is required to produce the desired film material. While it is conceptually possible to analyze a film for such a substance during deposition of the film, the fact that the deposition typically occurs from evaporation in a vacuum chamber renders this concept impractical since the necessary apparatus, unless of complex and presently non-existing construction, would be damaged by deposition on the apparatus or would not function under the conditions for deposition. As a result, it is necessary to transfer the deposited film and substrate through an environment sufficiently close to the usual ambient temperature and atmosphere that heretofore the substance escaped from the film or was replaced by a greater or lesser quantity of the substance present in the transfer environment.

More specifically, in the deposition of a thin layer of a well-known niobium/germanium compound, $Nb_3Ge$, where this compound is to have a desired structure which results in the layer becoming superconducting at a relatively high temperature, it has been found necessary that the deposition occur at about 900° C. and with oxygen present in the layer during deposition so that the desired structure is formed instead of some other niobium/germanium structure on. However, when the layer has cooled to about 500° C., the oxygen has diffused from the layer so that analysis thereof for oxygen would be useless insofar as determining the presence of oxygen during the actual deposition conditions.

SUMMARY OF THE INVENTION

The subject invention involves the deposition, on a first thin film layer which requires deposition in the presence of a substance which would otherwise escape from the layer prior to analysis of the layer for the substance, of a second layer, which captures the substance for subsequent analysis in the second layer, and involves the deposition on the second layer of a third layer which seals the second layer against entry of the substance from the environment.

It is an object of the present invention to provide a method for the determination of the presence of such a substance in the first layer during deposition of the substance in a substrate.

Another object is to provide a method using relatively simple and conventional apparatus in analysis for such a substance in a different vacuum chamber than that in which the first layer was deposited and after transfer of the films and substrate through the usual ambient terrestrial environment.

A further object is to provide such a method particularly useful for determining the presence of oxygen within a growing $Nb_3Ge$ film during vacuum deposition thereof at a relatively high temperature.

BRIEF DESCRIPTION OF THE DRAWING

Other objects, advantages and novel features of the method of the subject invention will become apparent from the following detailed description when considered with the accompanying drawing in which.

DETAILED DESCRIPTION OF THE INVENTION

Figure 1:
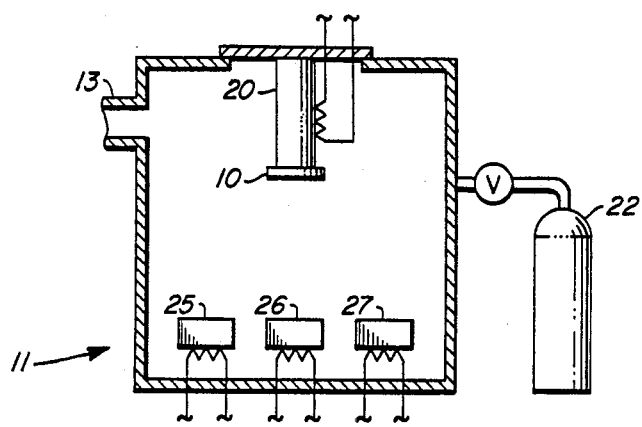
FIG. 1 is a diagram of a first vacuum chamber used to deposit thin film layers in the practice of the method.
Figure 2:
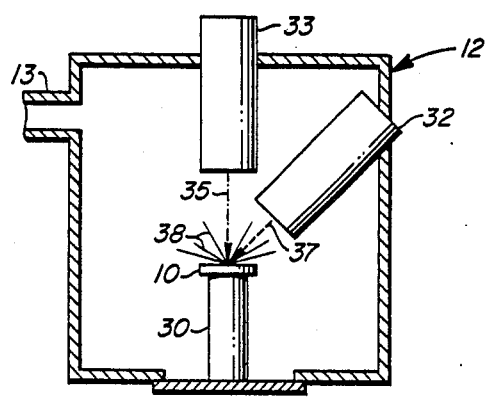
FIG. 2 is a diagram of a second vacuum chamber used in the practice of the method to analyze a film deposited in the chamber of FIG. 1.
Figure 3:
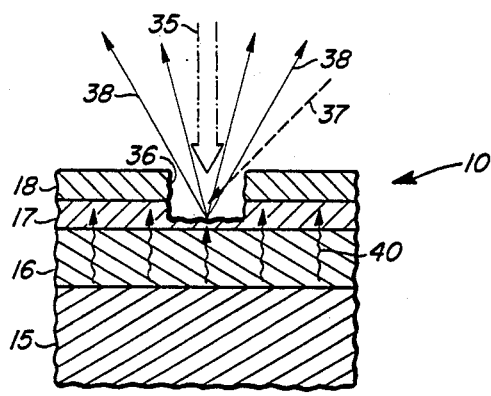
FIG. 3 is a greatly enlarged section of the layers, as deposited in the first chamber, undergoing analysis in the second chamber.

In the figures is shown a thin film structure 10 which is deposited in a first vacuum chamber 11, shown in FIG. 1, and which is analyzed in second vacuum chamber 12, shown in FIG. 2. Chambers 11 and 12 and their appurtances are of any suitable construction and are well known in the art of vacuum deposition and are, therefore, diagrammatically represented as typified by a vacuum pump connection 13 for each chamber. Film structure 10 is shown in FIG. 3 and, in a typical application of the subject invention as will be explained in greater detail, includes substrate 15 on which is deposited a first layer 16 of a desired first material, which typically is useful as a superconductor in electronic circuits, followed by direct deposition on the first layer of a continuous second or capture layer 17 of a second or retaining material on which is, in turn, directly deposited a continuous third or cap layer of a third or sealing material.

Chamber 11 has, as shown in FIG. 1, any suitable temperature controlled deposition mount 20 for removably mounting structure 10 within the chamber in a vacuum first environment at a predetermined relatively high deposition temperature. Chamber 11 is associated with a controllable source 22 of a substance, typically a gas, which must be present in layer 16 as this layer is deposited in such environment and at such temperature so that this layer is formed with the desired properties. Chamber 11 contains a first source 25 of a first evaporated material and a second source 26 of a second evaporated material. These evaporated materials, when deposited on substrate 15 in the environment of chamber 11 and at such temperature, combine to produce the desired first material forming layer 16. Chamber 11 contains a third source 27 which provides the material forming layer 17. Sources 25 through 27 utilize any suitable construction, such as a well-known e-beam system, which can be selectively and individually activated or deactivated to provide or to stop a flow of the corresponding material in evaporated form for deposition in a selected one of the layers 16–18.

Chamber 12, as shown in FIG. 2, has any suitable mount 30 for removably mounting structure 10 within this chamber for analysis of layer 17. This analysis is typically conducted in a well-known manner by any suitable Auger electron spectroscopy apparatus 32 as layer 17 and layer 18 are progressively exposed by sputter depth profiling, with noble gas ions from any suitable source 33 thereof. As seen in FIGS. 2 and 3, these ions issue from source 33 in a beam 35 which erodes in structure 10 a crater 36, FIG. 3, into which an electron beam 37 probes from apparatus 32 to excite Auger electrons, indicated by numeral 38. Some of the Auger electrons enter apparatus 32 for determination thereby of the elemental composition and variation thereof with depth of layer 17.

The present invention is effective when layer 16 is formed with the superconducting structure of niobium/germanium compound $Nb_3Ge$ as the desired material. In this event, substrate 15 is placed on mount 20 and installed in vacuum chamber 11 and the mount is arranged to maintain substrate 15 and layers 16 through 17 of structure 10 at a first temperature of substantially 900° C. as the layers are deposited. Source 22 is arranged to provide a flow of elemental oxygen, source 25 is arranged to provide evaporated niobium, source 26 is arranged to provide evaporated germanium, and source 27 is arranged to provide evaporated yttrium.

Sources 25 and 26 are then activated concurrently so that niobium and germanium are deposited together in the presence of a quantity of oxygen from source 22 so that $Nb_3Ge$ forms layer 16, typically, with a thickness in the order of one micron. Sources 25 and 26 are then deactivated and oxygen source 22 is turned off and oxygen remaining in chamber 11 outside of layer 16 is extracted through connection 13.

While substrate 15 and layer 16 remain in the vacuum environment of chamber 11 and at the deposition temperature of layer 16 so that the quantity of oxygen present in layer 16 as deposited remains in this layer, source 27 is activated to deposit yttrium over layer 16 and oppositely of substrate 15 to form layer 17. Layer 17, typically, has a thickness in the order of 200 to 300 Angstrom units to ensure that layer 16 is completely covered. Source 27 is then deactivated.

While substrate 15 and layers 16 and 17 remain in the vacuum environment of chamber 11 with source 22 turned off and sources 26 and 27 inactivated, niobium source 25 is reactivated to deposit the continuous cap layer 18 over layer 17 and oppositely of substrate 15. Layer 18 is thus formed of elemental niobium and, typically, has a thickness in the order of 200 to 300 Angstrom units to seal layer 17 and complete layered structure 10.

Subsequently, as layer 16 cools to about 500° C. in the vacuum environment of chamber 11 after layer 17 is deposited, the quantity of oxygen in layer 16 diffuses therefrom as gaseous elemental oxygen into the yttrium which forms layer 17. This diffusion is indicated in FIG. 3 by arrows 40 and occurs from layer 16 in a direction opposite of substrate 15. In layer 17, the yttrium, a material well-known as a "getter" for oxygen since yttrium forms a very stable oxide therewith in the range of temperatures from 900° C. through the usual ambient temperature, reacts with this quantity of oxygen so that this quantity is captured in layer 17 as the quantity escapes from layer 16.

Structure 10 may then be transferred from chamber 11 to chamber 12 through the usual ambient terrestrial environment and atmosphere and installed on mount 30 so that substrate 15 and layers 16 through 18 are received in chamber 12. Structure 10 is thus transferred to chamber 12 through a second environment which is at a second temperature which is lower than the first temperature of substantially 900° C. at which layers 16 and 17 were deposited.

When structure 10 is transferred though or otherwise subjected to the terrestrial atmosphere environment, niobium layer 18 seals yttrium layer 17 so that oxygen in the atmosphere is excluded therefrom and cannot increase the amount of oxygen in layer 17 above the quantity which diffused thereto from the $Nb_3Ge$ in layer 16. It is apparent that, if layer 17 was not so sealed, atmospheric oxygen would combine with the yttrium therein and, on subsequent analysis of layer 17, could not be distinguished from oxygen which came from layer 16.

When structure 10 is installed in the vacuum environment of chamber 12, layer 18 is penetrated by beam 35 and layer 17 is then analyzed by sputter depth profiling and Auger electron spectroscopy in the well-known manner previously described to determine the presence in layer 17 of the quantity of oxygen diffused thereto from layer 16 when the $Nb_3Ge$ of layer 16 was formed.

Obviously, many modification and variations of the present invention are possible in light of the above teachings. It is, therefore, to be understood that the invention may be practiced within the scope of the following claims other than as specifically described above. For example, other oxide forming elements than yttrium may be used to form layer 17, a mixture of yttrium and gadolinium being known to be effective for this purpose. It is apparent that the method of the present invention is effective to detect other gases than oxygen present in a layer during the formation of the layer from materials other than niobium and germanium. When it is desired to determine the former presence of a substance other than oxygen in a first layer such as 16, any suitable material may be used for a layer such as 17, which captures such other substance upon escape from the first layer. A cap layer, such as 18, may be formed of any suitable material to prevent contamination of a capture layer, such as 17, from the environment and, if required, to seal the capture layer against escape therefrom of the captured substance. It is, of course, advantageous to use niobium or another material as a sealing material when this material is also required to form a previously deposited layer. If no suitable sealing material such as niobium is already needed for deposition of a previous layer, the capture layer may be formed of gold or some other easily deposited and particularly non-reactive material.

What is claimed is:

1. A method for detecting a quantity of a substance in a layer deposited on a substrate, said quantity being present in a first layer of a first material during deposition at a first temperature of the first layer on the substrate in a vacuum first environment, by analysis of a layer deposited on the substrate and containing said quantity subsequent to transfer of the substrate together with any layer deposited thereon through a second environment which is at a second temperature lower than said first temperature and in which said quantity escapes from the first layer in a direction oppositely of the substrate, said second environment containing said substrate and such analysis being unable to distinguish between said quantity present during such deposition and said substance entering from the second environment into a layer deposited on the substrate and transferred therewith through the second environment, the method comprising the steps of:

depositing over said first layer, while the substrate and the first layer are in the first environment and at said first temperature, a continuous second layer of a second material which captures said quantity upon such escape thereof from the first layer;

depositing over the second layer oppositely thereof from the substrate, while the substrate, the first layer, and the second layer are in the first environment, a continuous third layer of a third material which seals the second layer form the second environment when the second layer is transferred thereinto together with the substrate and the first layer deposited thereon;

transferring the substrate, together with the first layer as deposited thereon, the second layer as deposited on the first layer, and the third layer as deposited on the second layer, through the second environment to means for analyzing the second layer for said substance so that said quantity escapes from the first layer and is captured in the second layer; and analyzing the second layer quantity by said analyzing means.

2. The method of claim 1 wherein the first environment is maintained within a first vacuum chamber and said second environment is the ambient terrestrial atmosphere, and wherein said analyzing means includes a second vacuum chamber for receiving the substrate, the first layer, the second layer, and the third layer.

3. The method of claim 2 wherein said analyzing means includes apparatus for sputter depth profiling of the second layer and for Auger electron spectroscopy to determine the presence therein of said quantity.

4. The method of claim 1 wherein said substance diffuses, at a temperature lower than said first temperature, from the first layer into the second layer, and wherein said second material is a material which forms a stable compound with said substance in a range of temperatures including said first temperature and said second temperature.

5. The method of claim 4 wherein said substance is gaseous, elemental oxygen and said compound is an oxide.

6. The method of claim 5 wherein said second material is yttrium.

7. The method of claim 4:
wherein the first layer after deposition consists substantially of a compound of niobium and germanium, said substance is oxygen, and the third layer consists substantially of elemental niobium;
wherein the first layer is deposited in a vacuum chamber from a first source which provides evaporated niobium and which is activated concurrently with a second source which provides evaporated germanium;
wherein said chamber contains a third source which provides said second material and which is activated to deposit the second layer following deposition of the first layer and subsequent deactivation of the first source and the second source; and
wherein said depositing of the third layer is performed by reactivating the first source with the second source remaining deactivated.

* * * * *